United States Patent [19]
Joseph

[11] Patent Number: 5,916,913
[45] Date of Patent: Jun. 29, 1999

[54] INHIBITION OF WOUND CONTRACTION WITH PACLITAXEL, COLCHICINE AND PENICILLAMINE

[76] Inventor: Hazel L. Joseph, 200 Winston Dr., Apt. 2806, Cliffside Park, N.J. 07010

[21] Appl. No.: 09/128,031

[22] Filed: Aug. 3, 1998

[51] Int. Cl.$^6$ ...................... A61K 31/335; A61K 31/195; A61K 31/16
[52] U.S. Cl. ........................... 514/449; 514/562; 514/629
[58] Field of Search ..................................... 514/449, 562, 514/629

[56] References Cited

U.S. PATENT DOCUMENTS 4,485,088  11/1984  Chvapil ..................................... 424/28

OTHER PUBLICATIONS

Damji, et al., Pharmacologic Modulation of Human Subconjunctival Fibroblast Behavior in Vitro, Ophthalmic. Surg., vol. 21, No. 1, pp. 31–43, 1990.
Ehrlich, et al., Evidence for the Involvment of Microtubules in Wound Contraction, Am. J. Surg., vol. 133, pp. 706–709, 1977.
Joseph et al., Inhibition of Wound Contraction with Colchicine and D–Penicillamine, Journal of Surgical Research, vol. 61, No. 1, pp. 197–200, 1996.
Rennard, et al., Colchicine Suppress the Release of Fibroblast Growth Factors from Alveolar Macrophages in Vitro, Am. Rev. Respir. Dis., vol. 137, pp. 181–185, 1988.
Rennekampff, et al., Reduction of Capsular Formation Around Silicon Breast Implants by D–D–Pencillamine in Rats, Scand. J. Plast. Reconstr. Surg. Hand. Sur., vol. 26, No. 3, pp. 253–255, 1992.
McGrath, et al, The Spatial and Temporal Quantification of Myofibroblasts, Plastic and Reconstructive Surgery, pp. 975–981, Jun. (1982).
Joseph et al. J. Surg. Res., 61 (1), 197–200 (Abstract), 1996.

*Primary Examiner*—Raymond Henley, III
*Attorney, Agent, or Firm*—Friscia & Nussbaum

[57] ABSTRACT

The present invention uses Paclitaxel and/or Colchicine in an appropriate carrier to inhibit wound contraction. Paclitaxel is an antimicrotubule agent that is currently used as a cancer chemotherapeutic drug. Colchicine inhibits microtubule dependent processes such as cell contraction and motility. It has been given orally for decades to treat gout. Previous studies using Colchicine to control wound contraction have been unsuccessful because of both local and systemic toxicity. Studies using the present invention demonstrate that Paclitaxel and Colchicine, when applied to wounds locally (either topically or by injection) in concentrations which are much lower than those previously studied, inhibit wound contraction, collagen deposition and granulation tissue growth. When combined with D-penicillamine, a drug that inhibits collagen cross-linking, the combination inhibits wound contraction, granulation tissue growth (nascent tissue that forms in the wound immediately post-injury), and intramuscular collagen deposition; epithelialization (sealing of the wound) is promoted.

13 Claims, 1 Drawing Sheet

INHIBITION OF WOUND CONTRACTION WITH PACLITAXEL, COLCHICINE AND PENICILLAMINE

BACKGROUND OF THE INVENTION

1. Field of the Invention

This invention relates to a method and composition for controlling scar formation and more particularly to the use of Paclitaxel and/or Colchicine and/or penicillamine for the inhibition of wound contraction and scar overgrowth while enhancing epithelialization.

2. Related Art

Wound contraction is the primary process by which wounds decrease their surface area over time. In World War I, contaminated wounds were allowed to heal secondarily by contraction resulting in reduced wound infection and sepsis. Wound contraction, however, frequently results in contractures and functional impairment, the extent of which depends upon the size and location of the wound. Previous studies using systemic or local drug therapy to inhibit contraction have produced inconsistent results, and there is not a single drug that is effective in controlling wound contraction clinically. Contractile fibroblasts and nascent collagen in granulation tissue have been implicated as having an important role in initiating and maintaining wound contraction. Ehrlich, et al. EVIDENCE FOR THE INVOLVEMENT OF MICROTUBULES IN WOUND CONTRACTION, Am. J. Surg., Vol 133, pages 706–709, 1977.

Colchicine has been administered orally to treat scleroderma and coronary restenosis, albeit with limited efficacy, primarily because of systemic toxicity associated with prolonged use of this drug. Colchicine has been shown to stimulate collagenase activity. Colchicine also inhibits many microtubule dependent processes including but not limited to fibroblast cell contraction and motility. Ehrlich, et al., applied Colchicine ($10^{-5}$M) topically to granulating wounds in rabbits and demonstrated that it inhibited contraction but resulted in local tissue death and a tendency towards infection. More recently, however, Rennard et al., COLCHICINE SUPPRESSES THE RELEASE OF FIBROBLAST GROWTH FACTORS FROM ALVEOLAR MACROPHAGES IN VITRO, Am. Rev. Respir. Dis. Vol 137(1), pages 181–185, 1988, demonstrated that Colchicine (40 ng/ml and 100 ng/ml) significantly inhibits secretion of two mediators of fibroblast proliferation (fibronectin and a macro-phage-derived growth factor) in vitro with detectable inhibition in the range of 1–10 ng/ml. The effect of Colchicine was not due to nonspecific toxicity since macrophages treated with Colchicine were capable of de novo protein synthesis and secretion of several protein products, despite the fact that fibronectin and growth factor release were suppressed. Notable also is the recent work of Damji et al., PHARMACOLOGIC MODULATION OF HUMAN SUBCONJUNCTIVAL FIBROBLAST BEHAVIOR IN VITRO, Ophthalmic. Surg., Vol. 21, No. 1, pages 31–43, 1990, who demonstrated that Colchicine inhibited cell migration at 0.004, μg/ml without cytotoxicity. These two studies prompted an evaluation of Colchicine, in vivo, at concentrations lower than $10^{-5}$M, administering the drug by local injection. It was postulated that by injecting Colchicine at low concentrations directly into the wound, the toxicity associated with applying the drug topically could be eliminated.

Penicillamine has been shown to demonstrate efficacy in the treatment of rheumatoid arthritis and Wilson's disease. It blocks cross-linking of newly formed tropocollagen and degrades a certain fraction of the more recently synthesized collagen. It has also been shown to have potent antiinflammatory properties. Rennekampiff et al., REDUCTION OF CAPSULAR FORMATION AROUND SILICON BREAST IMPLANTS BY D-D-PENICILLAMINE IN RATS, Scand. J. Plast. Reconstr. Surg. Hand. Sur. Vol. 26, No. 3, pages 253–255, 1992 demonstrated reduced capsular adhesion formation in rats around silicon implants using penicillamine in subcutaneously implanted osmotic minipumps. Penicillamine has been associated with the formation of less severe esophageal stricture in rabbits.

In the paper by Joseph. et al., INHIBITION OF WOUND CONTRACTION WITH COLCHICINE AND D-PENICILLAMINE, published Feb. 15, 1996 in the Journal of Surgical Research, Vol. 61, No. 1, pages 197–200, the effects of locally injected combined Colchicine and D-penicillamine on wound contraction were investigated in a murine model. The data suggested that very low concentrations of Colchicine and D-penicillamine only when combined and injected locally is potentially useful in controlling surface scar formation. The drugs used alone did not significantly alter scarring.

Another drug, Paclitaxel is a well-known chemotherapeutic drug for the treatment of various metastatic cancers. It has been approved by the Food and Drug Administration (FDA) for the treatment of ovarian and breast cancers and is currently in clinical trial for the treatment of lung and colon cancers.

The compound is a natural product primarily extracted from the bark of the PuYew tree, *Taxus brevifolia*, and also found in *T.baccata, T. walichiana* and *T. wunnanensis* and other biomass extracts from plant material. Aquataxul is also available from cultured plant cells and fungi.

U.S. Pat. No. 4,485,088 to Chvapil discloses a method of treating fibrotic lesions related to abnormal collagen polymerization by local administration of lathyrogen substance and D-penicillamine into the site of the injury. The lathyrogenic drugs are administered by local injection or onto the skin and percutaneously transported into the lesion.

Wounds heal by contraction and scar formation. Wound contraction is the process by which wounds decrease their surface area over time. Wound contraction however, frequently results in functional impairment because of the involvement of the adjacent tissues, the extent of which depends on the size and location of the wounds. The mechanisms of these processes are not completely understood; consequently, surgeons are unable to alter the outcome in most patients. In patients with large wounds, wounds on the face and burns, permanent disfigurement and lifelong functional limitations often result.

What is needed, and is not heretofore been developed is an effective combination of drugs which synergistically act or coact to control scar formation through the inhibition of wound contraction.

OBJECTS AND SUMMARY OF THE INVENTION

A principal object of the present invention is to provide a method of treating a wound.

Another object of the present invention is to provide a drug preparation for inhibiting wound contraction.

Another object and advantage of the present invention is to provide a method for treating a wound and a drug preparation which promotes epithelialization.

Still a further object and advantage of the present invention is to provide of method for treating a wound and a drug preparation to inhibit granulation tissue.

An additional object and advantage of the present invention is to provide a method for treating a wound and a drug preparation to inhibit excessive scar overgrowth.

Even an additional object and advantage of the present invention to provide a method for treating a wound and a drug preparation to inhibit intramuscular collagen deposition.

It is still a further object of the present invention to provide a drug including Paclitaxel and/or Colchicine and/or D-penicillamine for inhibiting wound contraction.

It is even an additional object of the present invention to provide drug to inhibit wound contraction which is injected or placed topically at the site of a wound.

The present invention uses Paclitaxel and/or Colchicine in an appropriate carrier to inhibit wound contraction. Paclitaxel is an agent that inhibits disassembly of the cell's microtubules that is essential for cell division and is currently used as a cancer chemotherapeutic drug. Colchicine inhibits microtubule dependent processes such as cell contraction and motility and has been given orally for decades to treat gout. Previous studies using Colchicine to control wound contraction have been unsuccessful because of both local and systemic toxicity. Studies using the present invention demonstrate that Paclitaxel and Colchicine, when applied to wounds locally (either topically or by injection) in concentrations which are much lower than those previously studied, inhibit wound contraction, collagen deposition and granulation tissue growth. When combined with penicillamine, a drug that is believed to inhibit collagen cross-linking, the combination enhances inhibition of wound contraction, granulation tissue growth (nascent tissue that forms in the wound immediately post-injury) collagen disposition in the wound; intramuscular collagen deposition additionally subjacent to the wound and; epithelialization (sealing of the wound) is promoted.

DETAILED DESCRIPTION OF THE INVENTION

Figure 1:
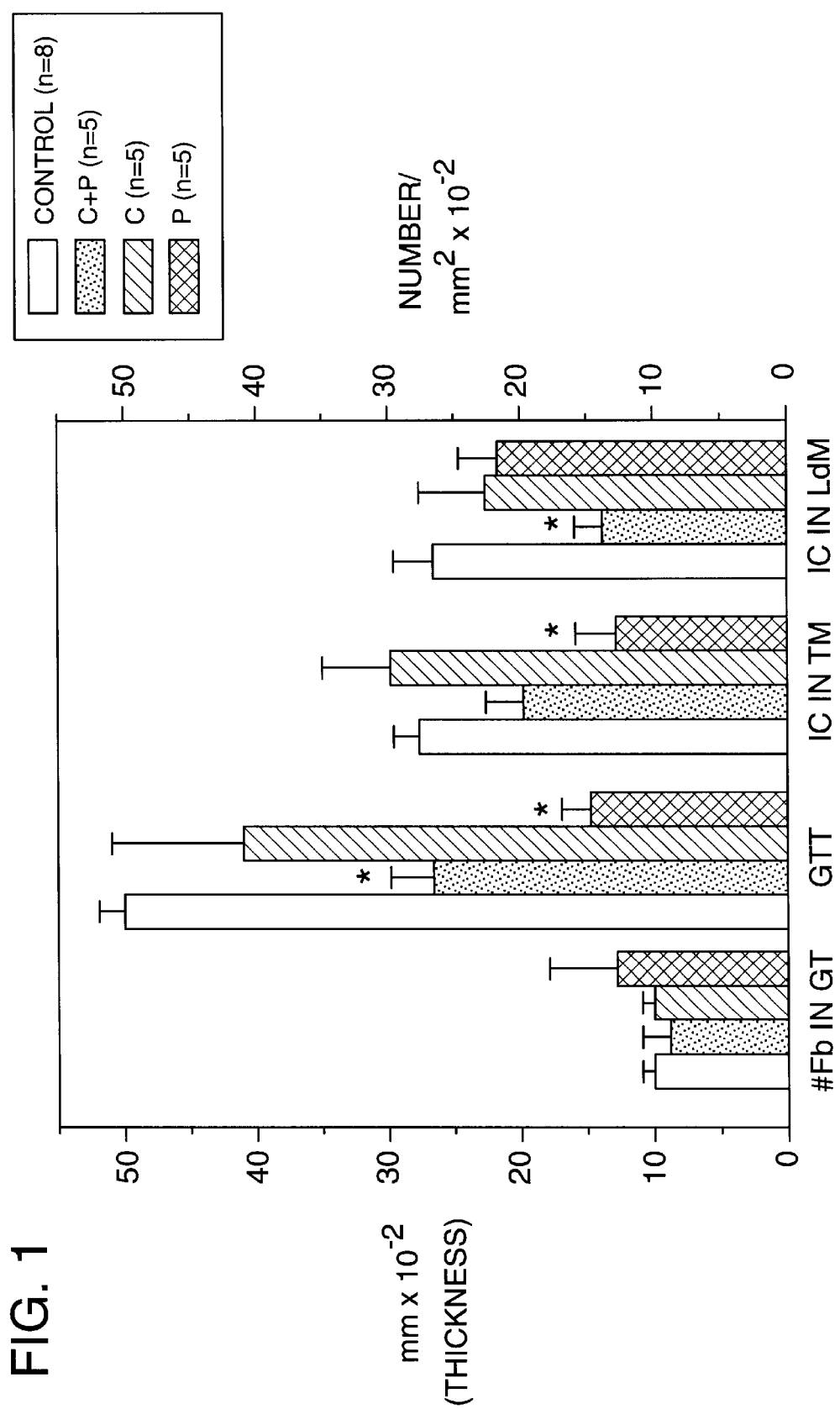
FIG. 1 is a graph comparing results of prior investigations on aspects of the invention. Comparison of granulation tissue, the number of fibroblasts in granulation tissue, and the number of inflammatory cells in subjacent muscles in animals treated for five days with normal saline (control), Colchicine, Penicillamine, or combined Colchicine and Penicillamine. Graph shows means ±SEM. One-way ANOVA with Duncan's post hoc test. $P \leq 0.0:5$ from control for all comparisons.

The present invention uses Paclitaxel and/or Colchicine in an appropriate carrier to inhibit wound contraction. Paclitaxel is an agent that inhibits disassembly of the cell's microtubules that is essential for mitosis. It is currently used as a cancer chemotherapeutic drug. Colchicine inhibits microtubule dependent processes such as cell contraction and motility and it has been given orally for decades to treat gout although it's mechanism of action is not clear. For decades, almost every drug imaginable has been evaluated for its potential role in wound healing. In fact, previous studies using Colchicine to control wound contraction have been unsuccessful because of both local and systemic toxicity. Currently, there is no single drug or drug combination that prevents scar formation. Studies using the present invention demonstrate that Paclitaxel and Colchicine, when applied to wounds locally (either topically or by injection) in concentrations which are much lower than those previously studied, inhibit wound contraction, collagen deposition and granulation tissue growth. When combined with D-penicillamine, a drug that is postulated to inhibit collagen cross-linking, the combination inhibits wound contraction, granulation tissue growth (nascent tissue that forms in the wound immediately post-injury), collagen deposition in the wound as well as intramuscular collagen deposition; epithelialization (sealing of the wound) is promoted.

To examine the effects of Paclitaxel, the drug was diluted in normal saline carrier. Male homozygous hairless (hr/hr) mice were used. Mice were anesthetized with ketamine hydrochloride for surgical procedures (see also METHODS, in the aforementioned paper by Joseph, et a.). Two symmetrical (1 $cm^{-2}$) wounds were made on the dorsum, one on either side of the midline; thus each animal served as its own control. A volume of 0.15 ml. of $10^{-5}$M Paclitaxel was injected into the wound on one side and 0.15 ml. normal saline (control) was injected into the wound on the other side daily for five days. The wounds were covered at all times and dressings were changed daily. To determine the rate of wound contraction, the border of each wound was traced daily. After determining the perimeter, the tracing was quantified using an IBM computer and digitizer pad to determine the area of the wound (Sigma Scan software application). This revealed that the Paclitaxel wounds were 30–35% larger than the control wounds indicating that wound contraction is inhibited by the drug. Wounds completely epithelialized, affirming a viable healthy wound bed and enhanced epithelialization. Wounds were thinner and smoother. In the presence of locally injected D-penicillamine (3 additional animals), the effect was more pronounced; wounds remained at nearly the original size of the injury. There was no gross evidence of wound infection or breakdown and no evidence of systemic toxicity. No animals demonstrated significant weight loss during the five day treatment period.

As discussed in the aforementioned paper by Joseph, et al., the effects of locally injected combined Colchicine and D-penicillamine on wound contraction have been investigated in a murine model. Two full-thickness excisional wounds were made on either side of the back of hairless (hr/hr) mice. A volume of 0.15 ml of Colchicine, D-penicillamine, or combined Colchicine and D-penicillamine in normal saline vehicle were injected daily into the wound on one side of the animal and 0.15 ml of vehicle alone was injected into the wound on the other side for 5 or 10 days; again, each animal served as its own control the surface area of each wound was measured on Days 0, 5, and 10 to determine an index of the rate of wound contraction. At the end of the experimental period (Day 5 or 10), wounds were excised en bloc from euthanized animals for histological studies. The following histological parameters were determined: the thickness of the granulation tissue, the number of fibroblasts in granulation tissue per unit area, and the number of inflammatory cells (neutrophils, lymphocytes, macrophages, mast cells) in subjacent muscle per unit area and collagen deposition in subadjacent muscle. The data showed that after 5 days of treatment, wound contraction was significantly inhibited only in wounds treated with combined Colchicine and D-penicillamine. Wound contraction was significantly inhibited even after 10 days of treatment with the combination. Histological studies revealed that although the thickness of the granulation tissue and the number of inflammatory cells in subjacent muscle were deceased by D-penicillamine alone, only combined Colchicine and D-penicillamine decreased the thickness of the granulation tissue, fibroblasts in granulation tissue, and inflammatory cells in subjacent muscle and collagen deposition in subadjacent muscle. Thus, very low concentrations of Colchicine and D-penicillamine, when combined and injected locally effectively controls scar formation.

The Figure is a graph comparing results of Joseph, et al. The Figure shows a comparison of granulation tissue, the number of fibroblasts in granulation tissue, and the number of inflammatory cells in subjacent muscles in animals treated for five days with normal saline (control), Colchicine, Penicillamine, or combined Colchicine and Penicillamine. Graph shows means ±SEM. One-way ANOVA with Duncan's post hoc test. $P \leq 0.05$ from control for all comparisons.

METHODS

Ketamine hydrochloride (1 mg/kg) anesthetized male homozygous hairless (hr/hr) mice (20–30 g, 6–8 weeks of age) were used. The Institutional Animal Care and Use Committee (IACUC) guidelines were strictly followed. The animals were kept in separate cages at room temperature (24° C.) and maintained on standard rodent chow and water ad libitum.

Wound Creation and Drug Application

Two full-thickness excisional wounds (1 cm$^2$) were made on the dorsum of each mouse, one on each side, 0.75 cm from the midline. Preliminary experiments demonstrated that contraction kinetics in bilateral symmetrical wounds in hairless mice are not significantly ($P \leq 0.05$) different: thus, comparing rates of contraction in two wounds on the same animal is a good internal control. The drug was injected into the wound on one side of the animal and normal saline (control) was injected into the wound on the other side of the animal. There was no set pattern (left side vs right side) for the test site and control. A small indelible ink mark on the hindlimb of each animal identified the side of the animal with the wound treated with drug. A volume of 0.15 ml of Colchicine ($10^{-6}$M) (Group C;n=7), D-penicillamine ($10^{-2}$M) (Group P;n=9), or Colchicine ($10^{-6}$M) plus D-penicillamine ($10^{-2}$M) (Group C+P; 5 days; n=9), Colchicine ($10^{-6}$M) plus D-penicillamine ($10^{-2}$M) (Group C+P; 10 days; n=6), or normal saline was injected into each wound daily. The wounds were covered at all times with sterile Vaseline gauze and Opsite overlay to prevent desiccation and contamination. Dressings were changed daily following injection of drug normal saline, surgical procedures, drug injections and dressing changes were done under aseptic conditions.

Wound Measurements

To determine the rate of contraction, the border of the each wound was traced with a fine point ink tracing pen (Pentel) on Arkwright transparency film on Days 0, 5, and 10 under a high magnification operating microscope. The perimeter of the wound that represented the advancing full-thickness margin was traced rather than the advancing epithelium. The area of the wound tracing was quantified using an IBM personal computer and digitizer pad (Sigma Scan software application). To determine the reliability of this measure, a known area was traced five consecutive times and the difference in the area (cm$^2$) measurement was found to be less than 0.02 cm$^2$ among all tracings. The percentage of contraction was determined according to the following formula:

$$P_n = \frac{Sa_i - Sa_n}{Sa_i} \times 100$$

where $P_n$ is percentage of contraction on Day n, $Sa_i$ is initial wound surface area and $Sa_n$ is wound surface area on Day n.

Light Microscopy

Following the experimental period (5 days), animals (randomly selected): five out of seven from Group C, five out of nine from Group P, and five out of none from Group C+P were euthanized with a pentobarbital overdoes (60 mg/kg, i.p.) for histological studies. From euthanized animals from Groups C, P, and C+P, eight normal saline treated wounds were randomly selected to be studied histologically. From Group C+P (treated for 10 days), four out of six animals were euthanized and both the Colchicine plus D-penicillamine treated wound and the normal saline treated wounds were studied histologically. Wounds were excised with the chest wall. A single strip of tissue spanning the central portion and edges of the wound was cut and embedded in paraffin (Paraplast X-tra, Oxford Labware, St. Louis, Mo.). Eight serial sections 5 $\mu$m thick were cut, mounted on slides, and stained with hematoxylin and eosin and Gormori's Trichrome. The orientation of the tissue in situ was maintained on the slides.

Granulation tissue thickness measurement. In each section, granulation tissue thickness was determined by measuring the vertical span of the granulation tissue in three regions of the wound: the lateral margin, halfway between the lateral margin and the center, and at the center of the wound. These results were averaged to determine the approximate granulation tissue thickness in each section.

Cell counts. In each section, fibroblast cells in 0.10 mm$^2$ field were counted at the center of the vertical span of the granulation tissue. This was repeated in three regions of each section: the lateral margin, halfway between the lateral margin and the center, and at the center of the wound. Similarly, inflammatory cells in a 0.10 mm$^2$ field were counted at the center of the vertical span of the trapezius muscle and at the center of the vertical span of the latissimus dorsi muscle; this was repeated along in three regions of the wound: at the lateral margin, halfway between the lateral margin and the center, and at the center of the wound. The number of cells from three fields were averaged to approximate the number of fibroblasts in granulation tissue, the number of inflammatory cells in the trapezius muscle, and the number of inflammatory cells in latissimus doris muscle in each slide section Statistics Data were statically analyzed using One-way ANOVA with Duncan's post hoc test to assess differences among groups and Student's t test when two groups were directly compared for any single variable. Data are reported as mean±SEM.

RESULTS

The rate of wound contraction was decreased after 5 days only in wounds treated with the combination of Colchicine and D-penicillamine (Table 1).

TABLE 1

Rates of Wound Contraction

| Group | n | Day | Size in relation to initial area (%) |
|---|---|---|---|
| C | 7 | 5 | 77 ± 5 |
| Control | 7 | 5 | 70 ± 5 |
| P | 9 | 5 | 70 ± 10 |
| Control | 9 | 5 | 65 ± 8 |
| C + P | 9 | 5 | 93 ± 5* |
| Control | 9 | 5 | 75 ± 5 |
| C + P | 6 | 10 | 57 ± 4* |
| Control | 6 | 10 | 36 ± 3 |

Note: C + P = colchicine plus D-penicillamine, C = colchicine, P = penicillamine.
*$P \leq 0.05$ from appropriate control (Student's paired t test).

The decreased rate of wound contraction was also significant after 10 days of treatment with combination. In contrast, the thickness of the granulation tissue was decreased in wounds treated with not only the combination of Colchicine and penicillamine, but also penicillamine alone. The number of fibroblasts in granulation tissue per unit area was also decreased in wounds treated with combined Colchicine and penicillamine, but only after 10 days. The number of inflammatory cells per unit area was decreased in subjacent muscle of wounds treated with combined Colchicine and D-penicillamine and in wounds treated with D-penicillamine alone. Table 2 summarizes the histological data.

TABLE 2

Histological Data

| Group | n | Day | GTT (mm × $10^{-2}$) | # Fb per (mm² × $10^{-2}$) | # IC per mm² × $10^{-2}$ (TM) | # IC per mm² × $10^{-2}$ (LdM) |
|---|---|---|---|---|---|---|
| C | 5 | 5 | 41 ± 10 | 4 ± 3 | 30 ± 5 | 23 ± 5 |
| P | 5 | 5 | 15 ± 2** | 13 ± 5 | 13 ± 3** | 22 ± 8 |
| C + P | 5 | 5 | 27 ± 3** | 9 ± 2 | 20 ± 3 | 14 ± 2** |
| Control | 8 | 5 | 50 ± 1 | 10 ± 1 | 28 ± 2 | 27 ± 3 |
| C + P | 4 | 10 | 15 ± 1* | 10 ± 1* | — | — |
| Control | 4 | 10 | 27 ± 5 | 18 ± 3 | — | — |

Note: C + P = colchicine plus D-Penicillamine, C = colchicine, P = D-penicillamine, # Fb = number of fibroblast cells, GTT = granulation tissue thickness, # IC = number of inflammatory cells, TM = trapezius muscle, LdM = *latissimus dorsi* muscle.
*P = 0.05 from appropriate control (Student's paired t test).
**P = 0.05 from appropriate control (One-way ANOVA with Duncan's post hoc test).

DISCUSSION

Contraction was significantly inhibited in wounds treated with combined Colchicine and D-penicillamine for 5–10 days. This inhibition may be due to the cumulative effects of both drugs. McGrath, et al., THE SPATIAL AND TEMPORAL QUANTIFICATION OF MYOFIBROBLAST, Plast. Reconstr. Surg., Vol. 69, No. 6., pages 975–985, 1982, demonstrated that when the mean number of myofibroblasts (contractile fibroblasts) in the wound is highest the greatest reduction in the wound area takes place. It was observed that the number of fibroblasts in granulation tissue is deceased in wounds treated with combined Colchicine and D-penicillamine. This supports McGrath's finding suggesting there may be an association between the amount of wound contraction and the number of fibroblasts in granulation tissue. The histological studies of wounds treated with Colchicine alone and D-penicillamine, the reduction in the number of fibroblasts in granulation tissue may be predominately due to Colchicine (The Figure). Although, the number of inflammatory cells in subjacent muscle was decreased ($P \leq 0.05$) in wounds treated with D-penicillamine alone. The data does not suggest that D-penicillamine is responsible for the decreased number of inflammatory cells in subjacent muscle in wounds treated with combined Colchicine and D-penicillamine.

Toxic compounds produce histological changes such as a violent inflammatory response with cellular debris or morphologically abnormal cells. These features were not observed in wounds treated with normal saline or drug(s) suggesting that the effects of combined Colchicine and D-penicillamine at the concentrations tested were not due to cytotoxicity. Epithelialization occurred in wounds treated with Colchicine, D-penicillamine, or combined Colchicine and D-penicillamine. Clinically, this is significant because "islands" of epithelialization in healthy appearing granulation tissue are one of the most reliable indicators of a viable wound bed and absence of wound infection. A treatment modality that inhibits wound contraction while allowing epithelialization potentially has practical usage as a locally or topically applied adjuvant in skin grafting regimens.

CONCLUSIONS

The combination of Colchicine and penicillamine, when injected locally into granulating wounds in a murine model, exerts a measurable inhibitory effect on wound contraction. At the concentrations tested, signs of toxicity were not observed grossly or histologically in wounds treated with Colchicine, penicillamine, or combined Colchicine and penicillamine. The data suggests that combined Colchicine and penicillamine, when applied locally, is a useful modality for controlling scar formation.

The work of Joseph et al., has demonstrated that colchicine and Paclitaxel, when combined with penicillamine is an effective means of limiting scarring or improving the aesthetic and functional outcome of scar formation. These are the first studies that show that by combining these drugs, very low concentrations can be used that are non-toxic to the tissue yet therapeutic with minimal or no systemic side effects.

Having thus described the invention in detail, it is to be understood that the foregoing description is not intended to limit the spirit and scope thereof. What is desired to be protected by Letters Patent is set forth in the appended claims.

What is claimed is:

1. A method of treating a wound comprising:
    providing a drug preparation containing Paclitaxel in a drug carrier; and
    applying a therapeutically effective amount of the drug preparation locally to a wound site.

2. The method of claim 1 wherein the drug preparation further includes penicillamine.

3. The method of claim 1 wherein the drug preparation is applied either topically or by injection.

4. The method of claim 1 wherein the drug preparation further includes d-penicillamine.

5. The method of claim 1 wherein the drug preparation further includes Colchicine.

6. The method of claim 5 wherein the drug preparation further includes d-penicillamine.

7. A method of treating a wound comprising:
    providing a drug preparation containing Paclitaxel and penicillamine and in a drug carrier; and
    applying a therapeutically effective amount of the drug preparation locally to a wound site.

8. The method of claim 7 wherein the drug preparation further includes Colchicine.

9. The method of claim 7 wherein the drug preparation is applied either topically or by injection.

10. The method of claim 7 wherein said penicillamine is d-penicillamine.

11. A drug preparation for treating wounds, said preparation consisting essentially of a drug carrier, and effective amounts of Paclitaxel and penicillamine.

12. The drug preparation of claim 11 further including an effective amount of coichicine.

13. The drug preparation of claim 11 wherein said penicillamine is d-penicillamine.

* * * * *